US012733604B2

(12) United States Patent
Haarsma et al.

(10) Patent No.: US 12,733,604 B2
(45) Date of Patent: Sep. 15, 2026

(54) TROPICAL ROOT-KNOT NEMATODE RESISTANT CARROT PLANT

(71) Applicant: Bejo Zaden B.V., Warmenhuizen (NL)

(72) Inventors: Adriana Dorien Haarsma, Warmenhuizen (NL); Diana Katschnig, Warmenhuizen (NL); Willem Arie Zwaan, Warmenhuizen (NL); Peter Arnoldus Dekker, Warmenhuizen (NL); Albertus Johannes Maria Schrijver, Warmenhuizen (NL)

(73) Assignee: Bejo Zaden B.V., Warmenhuizen (NL)

( * ) Notice: Subject to any disclaimer, the term of this patent is extended or adjusted under 35 U.S.C. 154(b) by 186 days.

(21) Appl. No.: 18/694,470

(22) PCT Filed: Sep. 23, 2021

(86) PCT No.: PCT/EP2021/076245
§ 371 (c)(1),
(2) Date: Mar. 22, 2024

(87) PCT Pub. No.: WO2023/046288
PCT Pub. Date: Mar. 30, 2023

(65) Prior Publication Data

US 2024/0381823 A1 Nov. 21, 2024

(51) Int. Cl.

| | |
|---|---|
| ***A01H 6/06*** | (2018.01) |
| ***A01H 1/00*** | (2006.01) |
| ***A01H 5/06*** | (2018.01) |
| ***C12N 15/82*** | (2006.01) |
| ***C12Q 1/6895*** | (2018.01) |

(52) U.S. Cl.
CPC ........... *A01H 6/068* (2018.05); *A01H 1/1265* (2021.01); *A01H 5/06* (2013.01); *C12N 15/8205* (2013.01); *C12Q 1/6895* (2013.01)

(58) Field of Classification Search
CPC ................................. A01H 6/06; A01H 6/068
USPC ......................................................... 800/295
See application file for complete search history.

(56) References Cited

PUBLICATIONS

Aamir et al., "Inheritance and Mapping of Mj-2, a New Source of Root-knot Nematode (*Meloidogyne javanica*) Resistance in Carrot," Journal of Heredity, 2014, pp. 288-291, vol. 105.

Boiteux et al., "RAPD linkage map of the genomic region encompassing the root-knot nematode (*Meloidogyne javanica*) resistance locus in carrot," Ther. Appln. Genet., 2000, pp. 439-446, vol. 100.

Parsons et al., "Meloidogyne incognita nematode resistance QTL in carrot," Mol. Breeding, 2015, pp. 1-11, vol. 35.

Seo et al., "Screening and Histopathological Characterization of Korean Carrot Lines for Resistance to the Root-Knot Nematode Meloidogyne incognita," The Plant Pathology Journal, 2014, pp. 75-81, vol. 30(1).

Simon et al., "Evidence for simply inherited dominant resistance to Meloidogyne javanica in carrot," Theor. Appln. Genet., 2000, pp. 735-742, vol. 100.

*Primary Examiner* — Gary Benzion
(74) *Attorney, Agent, or Firm* — The Webb Law Firm

(57) ABSTRACT

The present invention relates to tropical root-knot nematode resistant carrot plants comprising a first tropical root-knot nematode resistance providing genomic fragment. The present invention further relates to methods for identifying tropical root-knot nematode resistant carrot plants, methods for providing tropical root-knot nematode resistant carrot plants and means for identifying tropical root-knot nematode resistant carrot plants.

14 Claims, No Drawings

Specification includes a Sequence Listing.

SEQUENCE LISTING

<160> NUMBER OF SEQ ID NOS: 40

<210> SEQ ID NO 1
<211> LENGTH: 101
<212> TYPE: DNA
<213> ORGANISM: Daucus carota

<400> SEQUENCE: 1
tgtttgagac tcwactcttc tcctttacca acgaaagtat ttatttgtga gcaatctttc 60
atgtcaaacc tagcaagtac cttctcaata tggctctttt a 101

<210> SEQ ID NO 2
<211> LENGTH: 101
<212> TYPE: DNA
<213> ORGANISM: Daucus carota

<400> SEQUENCE: 2
tgtttgagac tcwactcttc tcctttacca acgaaagtat ttatttgtga acaatctttc 60
atgtcaaacc tagcaagtac cttctcaata tggctctttt a 101

<210> SEQ ID NO 3
<211> LENGTH: 71
<212> TYPE: DNA
<213> ORGANISM: Daucus carota

<400> SEQUENCE: 3
tcctatctct cttcctcctc acaatccttc ccattctcca ctccttacca gccataccag 60
acccaaccac a 71

<210> SEQ ID NO 4
<211> LENGTH: 71
<212> TYPE: DNA
<213> ORGANISM: Daucus carota

<400> SEQUENCE: 4
tcctatctct cttcctcctc acaatccttc ccattctaca ctccttacca gccataccag 60
acccaaccac a 71

<210> SEQ ID NO 5
<211> LENGTH: 101
<212> TYPE: DNA
<213> ORGANISM: Daucus carota

<400> SEQUENCE: 5
attatactta tacttgttta aatatgtggt aactttgggt gccaatcact agagcaaatt 60
tttatgtaaa agttgtcaaa aatacaaaca aagrgagaga a 101

<210> SEQ ID NO 6
<211> LENGTH: 101
<212> TYPE: DNA
<213> ORGANISM: Daucus carota

<400> SEQUENCE: 6
attatactta tacttgttta aatatgtggt aactttgggt gccaatcact ggagcaaatt 60
tttatgtaaa agttgtcaaa aatacaaaca aagrgagaga a 101

<210> SEQ ID NO 7
<211> LENGTH: 101
<212> TYPE: DNA
<213> ORGANISM: Daucus carota

<400> SEQUENCE: 7
cttcacaact atttachaag taatttaaaa cttctttaat ctgtgaagct cgatatctta 60
ttgctttaac tcctataacc cgacwttctc aacatatttc t 101

<210> SEQ ID NO 8
<211> LENGTH: 101
<212> TYPE: DNA
<213> ORGANISM: Daucus carota

<400> SEQUENCE: 8
cttcacaact atttachaag taatttaaaa cttctttaat ctgtgaagct tgatatctta 60
ttgctttaac tcctataacc cgacwttctc aacatatttc t 101

<210> SEQ ID NO 9
<211> LENGTH: 71
<212> TYPE: DNA
<213> ORGANISM: Daucus carota

<400> SEQUENCE: 9
cgaccaatga tatcagtttt ttcgacgata ataatctcgg gtcgttagaa ttggattctc 60
tctggacttg a 71

<210> SEQ ID NO 10
<211> LENGTH: 71
<212> TYPE: DNA
<213> ORGANISM: Daucus carota

<400> SEQUENCE: 10
cgaccaatga tatcagtttt ttcgacgata ataatcttgg gtcgttagaa ttggattctc 60
tctggacttg a 71

<210> SEQ ID NO 11
<211> LENGTH: 101
<212> TYPE: DNA
<213> ORGANISM: Daucus carota

<400> SEQUENCE: 11
ttatatactg tataaaacaa tgattagtgc aacaaaaatt agtgatagtc atagttataa 60
atactggtaa ggaaactagt ttttagtttg tatttaagag t 101

<210> SEQ ID NO 12
<211> LENGTH: 101
<212> TYPE: DNA
<213> ORGANISM: Daucus carota

<400> SEQUENCE: 12
ttatatactg tataaaacaa tgattagtgc aacaaaaatt agtgatagtc gtagttataa 60
atactggtaa ggaaactagt ttttagtttg tatttaagag t 101

<210> SEQ ID NO 13
<211> LENGTH: 71
<212> TYPE: DNA
<213> ORGANISM: Daucus carota

<400> SEQUENCE: 13
atccgtcaat tagaaaaagt taaaaaacac tctctctaga cacccattct catttgaagc 60
aacacgtgat g 71

<210> SEQ ID NO 14
<211> LENGTH: 71
<212> TYPE: DNA
<213> ORGANISM: Daucus carota

<400> SEQUENCE: 14
atccgtcaat tagaaaaagt taaaaaacac tctctctgga cacccattct catttgaagc 60
aacacgtgat g 71

<210> SEQ ID NO 15
<211> LENGTH: 101
<212> TYPE: DNA
<213> ORGANISM: Daucus carota

<400> SEQUENCE: 15
gctacaactt ttatcttttt cagtctttac atgaagtamt agccgtaaat tttkcaagcc 60
aaaggtgcaa cacattgtag actcgacaat atctttcact c 101

<210> SEQ ID NO 16
<211> LENGTH: 101
<212> TYPE: DNA
<213> ORGANISM: Daucus carota

<400> SEQUENCE: 16
gctacaactt ttatcttttt cagtctttac atgaagtamt agccgtaaat cttkcaagcc 60
aaaggtgcaa cacattgtag actcgacaat atctttcact c 101

<210> SEQ ID NO 17
<211> LENGTH: 101
<212> TYPE: DNA
<213> ORGANISM: Daucus carota

<400> SEQUENCE: 17
cacttgtcct gaagaatgtc aaggcaaata ttcccatact ggtcaacatt tggatggaag 60
cacattgtct caaacttcac ttggggaggc ttgaaaggat a 101

<210> SEQ ID NO 18
<211> LENGTH: 101
<212> TYPE: DNA
<213> ORGANISM: Daucus carota

<400> SEQUENCE: 18
cacttgtcct gaagaatgtc aaggcaaata ttcccatact ggtcaacatt gggatggaag 60
cacattgtct caaacttcac ttggggaggc ttgaaaggat a 101

<210> SEQ ID NO 19
<211> LENGTH: 101
<212> TYPE: DNA
<213> ORGANISM: Daucus carota

<400> SEQUENCE: 19
taaggcttgc rttggmttaa aragttgcag catcgacgta tcagtgtcaa cttttgggaa 60
tccgtgtaga ggagttacaa agagtttagc agtagaagcw t 101

<210> SEQ ID NO 20
<211> LENGTH: 101
<212> TYPE: DNA
<213> ORGANISM: Daucus carota

<400> SEQUENCE: 20
taaggcttgc rttggmttaa aragttgcag catcgacgta tcagtgtcaa tttttgggaa 60
tccgtgtaga ggagttacaa agagtttagc agtagaagcw t 101

<210> SEQ ID NO 21
<211> LENGTH: 101
<212> TYPE: DNA
<213> ORGANISM: Daucus carota

<400> SEQUENCE: 21

```
atgacaccaa cacggtgaaa gtcagtgtat ctggcctttt ggaggtggat ttgaaggtga     60

ctccaataaa agaaaaggaa aacaaggtgc acaactacca g                        101


<210> SEQ ID NO 22
<211> LENGTH: 101
<212> TYPE: DNA
<213> ORGANISM: Daucus carota

<400> SEQUENCE: 22

atgacaccaa cacggtgaaa gtcagtgtat ctggcctttt ggaggtggat gtgaaggtga     60

ctccaataaa agaaaaggaa aacaaggtgc acaactacca g                        101


<210> SEQ ID NO 23
<211> LENGTH: 71
<212> TYPE: DNA
<213> ORGANISM: Daucus carota

<400> SEQUENCE: 23

ccatacccat tcttttgaaa tgaaaatgca aaacagaagt cttccagtag ctctctacct     60

gcatttgaca a                                                          71


<210> SEQ ID NO 24
<211> LENGTH: 71
<212> TYPE: DNA
<213> ORGANISM: Daucus carota

<400> SEQUENCE: 24

ccatacccat tcttttgaaa tgaaaatgca aaacagaggt cttccagtag ctctctacct     60

gcatttgaca a                                                          71


<210> SEQ ID NO 25
<211> LENGTH: 71
<212> TYPE: DNA
<213> ORGANISM: Daucus carota

<400> SEQUENCE: 25

aaacattaaa cttggcggat gatgatatat ataatgccgt gctacttgtt gcagctgctt     60

ataatcactt t                                                          71


<210> SEQ ID NO 26
<211> LENGTH: 71
<212> TYPE: DNA
<213> ORGANISM: Daucus carota

<400> SEQUENCE: 26

aaacattaaa cttggcggat gatgatatat ataatgcggt gctacttgtt gcagctgctt     60

ataatcactt t                                                          71


<210> SEQ ID NO 27
<211> LENGTH: 71
<212> TYPE: DNA
<213> ORGANISM: Daucus carota

<400> SEQUENCE: 27

gatcgaaggg ggtgcggcca gaggtctttg cccgagcgta tgcccgtgtc ttctcctcgt     60

tacttgtcct t                                                          71


<210> SEQ ID NO 28
<211> LENGTH: 71
```

<212> TYPE: DNA
<213> ORGANISM: Daucus carota

<400> SEQUENCE: 28
gatcgaaggg ggtgcggcca gaggtctttg cccgagcata tgcccgtgtc ttctcctcgt 60
tacttgtcct t 71

<210> SEQ ID NO 29
<211> LENGTH: 71
<212> TYPE: DNA
<213> ORGANISM: Daucus carota

<400> SEQUENCE: 29
ctctcggrac ccaaccaatt accctacgaa ctttctcctc gaagagtact acacatgttt 60
ttgctgcctc a 71

<210> SEQ ID NO 30
<211> LENGTH: 71
<212> TYPE: DNA
<213> ORGANISM: Daucus carota

<400> SEQUENCE: 30
ctctcggrac ccaaccaatt accctacgaa ctttctcatc gaagagtact acacatgttt 60
ttgctgcctc a 71

<210> SEQ ID NO 31
<211> LENGTH: 71
<212> TYPE: DNA
<213> ORGANISM: Daucus carota

<400> SEQUENCE: 31
gagaatctgc cgtacggcgt gttcaagcct gacgaatgtt cggcacctcg acctggcgtt 60
gctatcggrg a 71

<210> SEQ ID NO 32
<211> LENGTH: 71
<212> TYPE: DNA
<213> ORGANISM: Daucus carota

<400> SEQUENCE: 32
gagaatctgc cgtacggcgt gttcaagcct gacgaatctt cggcacctcg acctggcgtt 60
gctatcggrg a 71

<210> SEQ ID NO 33
<211> LENGTH: 71
<212> TYPE: DNA
<213> ORGANISM: Daucus carota

<400> SEQUENCE: 33
gccaaaggct actacaaagt ggttgcaagt ttcaaaattg atgcacaagg gtgctgtgtc 60
aagtgaagat c 71

<210> SEQ ID NO 34
<211> LENGTH: 71
<212> TYPE: DNA
<213> ORGANISM: Daucus carota

<400> SEQUENCE: 34
gccaaaggct actacaaagt ggttgcaagt ttcaaaactg atgcacaagg gtgctgtgtc 60

-continued

```
aagtgaagat c                                                          71


<210> SEQ ID NO 35
<211> LENGTH: 71
<212> TYPE: DNA
<213> ORGANISM: Daucus carota

<400> SEQUENCE: 35

gaaaatatca tcgccacgag ataatttttg ctgatcaaca aagacttgag agtaacattc     60

gacttcccgt g                                                          71


<210> SEQ ID NO 36
<211> LENGTH: 71
<212> TYPE: DNA
<213> ORGANISM: Daucus carota

<400> SEQUENCE: 36

gaaaatatca tcgccacgag ataatttttg ctgatcagca aagacttgag agtaacattc     60

gacttcccgt g                                                          71


<210> SEQ ID NO 37
<211> LENGTH: 71
<212> TYPE: DNA
<213> ORGANISM: Daucus carota

<400> SEQUENCE: 37

ttttacatag ttacaattag aaattcagat cccacctttt agactccaac ctctccggct     60

aacttgaaag g                                                          71


<210> SEQ ID NO 38
<211> LENGTH: 71
<212> TYPE: DNA
<213> ORGANISM: Daucus carota

<400> SEQUENCE: 38

ttttacatag ttacaattag aaattcagat cccacctctt agactccaac ctctccggct     60

aacttgaaag g                                                          71


<210> SEQ ID NO 39
<211> LENGTH: 71
<212> TYPE: DNA
<213> ORGANISM: Daucus carota

<400> SEQUENCE: 39

tacaactcga tgcttatata tcacgaaaag aactcttcaa ggcagaagca aaatattgga     60

atgaaataat a                                                          71


<210> SEQ ID NO 40
<211> LENGTH: 71
<212> TYPE: DNA
<213> ORGANISM: Daucus carota

<400> SEQUENCE: 40

tacaactcga tgcttatata tcacgaaaag aactctttaa ggcagaagca aaatattgga     60

atgaaataat a                                                          71
```

TROPICAL ROOT-KNOT NEMATODE RESISTANT CARROT PLANT

CROSS-REFERENCE TO RELATED APPLICATION

This application is the United States national phase of International Application No. PCT/EP2021/076245 filed Sep. 23, 2021, the disclosure of which is hereby incorporated by reference in its entirety.

REFERENCE TO A SEQUENCE LISTING

The Sequence Listing associated with this application is filed in electronic format via Patent Center and is hereby incorporated by reference into the specification in its entirety. The name of the text file containing the Sequence Listing is 2401492_ST25.txt. The size of the file is 9,330 bytes, and the file was created on Mar. 8, 2024.

BACKGROUND OF THE INVENTION

Field of the Invention

The present invention relates to carrot plants with one or two tropical root-knot nematode resistance providing genomic fragments. The present invention further relates to methods for identifying tropical root-knot nematode resistant carrot plants, methods for providing tropical root-knot nematode resistant carrot plants and means for identifying tropical root-knot nematode resistant carrot plants. The present invention also relates to seeds, plant parts, and especially edible plant parts of the present plants.

Carrot, or *Daucus carota*, is a cultivated plant from the Umbelliferae (or Apiaceae) family, which is common in many parts of the world. The Umbelliferae family encompasses more than 3,500 species, including next to the genus *Daucus*, various other cultivated plants, for example, caraway, celery, coriander, dill, fennel, parsley, and parsnip.

Wild carrot, *Daucus carota* L., is endemic to large parts of the world. It has a white taproot that is initially edible but becomes woody after prolonged growth. The cultivated carrot, *Daucus carota*, and especially *Daucus carota* ssp. *sativus* is a root vegetable that is usually orange, but purple, red, yellow, and white varieties are also known.

In moderate climate zones, *Daucus carota* is a biennial plant that grows vegetatively in the first year after sowing. After overwintering, the plant will flower in the second year of cultivation. In tropical and subtropical areas, the carrot plant has an annual life cycle, and the shift from vegetative to generative growth occurs without vernalization.

Two types of male sterility are described in the genus *Daucus*. In the so-called brown anther type, anthers degenerate and shrivel before they can spread pollen. In the petaloid type, the stamens are replaced by petal-like structures.

Male sterility observed in cultivated carrots is generally due to cytoplasmic male sterility caused by mitochondrial defects. Since mitochondria are transferred to the offspring by egg cells only, this trait is maternally inherited. Male sterility is a useful trait in carrot breeding as it enables 100% cross-pollination. As a result, hybrids of *Daucus* are readily produced. Moreover, heterosis, or hybrid vigour, can be very strong in carrot.

Carrot is cultivated for its nutritious taproot. A major part of this root consists of an outer phloem cortex and an inner xylem core. Moreover, a large proportion of the cortex relative to the core is considered to have high horticultural quality. The taproot is rich in carotene, especially β-carotene, an important antioxidant that can be metabolized to vitamin A. Carrots are also a source of dietary fibre, vitamins C, B6, and K, and the antioxidant falcarinol. Antioxidants (including carotenoids) have been studied for their ability to prevent chronic disease.

The root length of carrot plants varies from 5 up to 40 cm, while the diameter can vary between 1 to 10 cm. Taproots also come in various shapes. Round, conical, or more cylindrical shapes are preferred depending on the purpose. The taproot of wild varieties is white, but cultivated carrots are ordinarily orange, sometimes red, purple, black, or yellow.

Cultivation of carrots occurs globally. In 2011, more than 35 million tons of carrots were produced. Yet, many pests are known that threaten harvests around the globe. These include bacterial, fungal, viral, and viroid diseases, but also insect and nematode pests. Major bacterial and fungal diseases are caused by, among others, *Xanthomonas hortorum, Erwinia carotovora, Alternaria dauci, Alternaria radicina, Pythium* spp., *Rhizoctonia* spp., *Sclerotinia* spp., *Fusarium* spp, *Botrytis cinerea*, and *Phytophthora* spp. Nematodes, such as *Heterodera carotae, Meloidogyne* spp. and *Pratylenchus* spp., cause severe damage to the taproot, resulting in yield loss and a product unsuitable for market. These yield losses have led to dedicated breeding programs by companies and governmental institutes to introduce genetic resistances in carrot plants against these various pathogens.

Root-knot nematodes of the genus *Meloidogyne* are examples of pests that significantly impact carrot cultivation. Root-knot nematodes cause an estimated annual loss of up to roughly $157 billion. These obligate plant-parasites have a worldwide distribution and a broad host range, including many important vegetable crops, particularly tomato, aubergine, okra, cucumber, melon, carrot, gourds, lettuce, and peppers. The genus *Meloidogyne* includes more than 90 species, but *Meloidogyne arenaria, Meloidogyne javanica, Meloidogyne incognita*, and *Meloidogyne hapla* are considered the economically most important species. The species *Meloidogyne hapla* occurs predominantly in cooler climates, and *Meloidogyne arenaria, Meloidogyne javanica* and *Meloidogyne incognita*, are present in warmer regions, in particular areas with tropical and sub-tropical climates and are referred to as tropical root-knot nematodes.

Once the carrot plant is infested with tropical root-knot nematodes, numerous galls form on the taproot and secondary roots. Galls are abnormal outgrowths of plant tissues. The taproot of the carrot plant can become forked, and the growth of the carrot plant stunted. The galling and forking of the storage root leads to a malformed carrot, which, although still edible, is unacceptable for market. The amount of galling and forking is directly linked to nematode pressure and is worsened by warmer weather when the nematodes are more active. Yield and market losses can be significant. For example, losses of up to 50% have been reported in southern regions of India.

Description of Related Art

The use of soil-applied nematicides is one effective approach to preventing *Meloidogyne* spp. infections. However, this approach is laborious and expensive. Moreover, the use of pesticides is increasingly restrained and organically grown vegetables are becoming increasingly popular.

Crop rotations and non-chemical management, including biological control organisms, can only control tropical root-knot nematodes to a limited extent, due to the wide host range of the nematodes, which includes many weeds. As a result, rotation options are limited.

The use of genetically resistant carrot varieties is the most efficient manner to prevent infection by tropical root-knot nematodes. Several resistances to *Meloidogyne javanica* and *Meloidogyne incognita* in carrot plants have been described in the prior art.

For example, two resistance loci that provide resistance to *Meloidogyne javanica* have been mapped to chromosome 8. The first locus was designated the Mj-1 locus and was discovered in the carrot cultivar Brasilia, in particular the line Br1252. The resistance provided by the Mj-1 locus is nearly completely dominant. The locus also provides partial resistance to *Meloidogyne incognita*. The second locus was designated Mj-2 and was discovered in the Chinese cultivar Ping Ding, also known as PI 652188. The Mj-2 locus has an incompletely dominant pattern of inheritance. Preliminary results suggest that this locus may also provide some resistance to *Meloidogyne incognita.*

In addition, Parsons et al. 2014 mapped resistance to *Meloidogyne incognita* in various carrot cultivars, in particular Brasilia from Brazil (Br1091), Homs from Syria, and the European cultivar Scarlet Fancy x Favourite (SFF). Resistance loci were identified on chromosomes 1, 2, 4, 8, and 9 in these cultivars (see Table 1). These loci are quantitative trait loci (QTLs) that each contribute small amounts to the overall resistance of the plant. As a result, it is necessary to combine several QTLs to provide carrots with an effective resistance against *Meloidogyne incognita* and *Meloidogyne javanica*. Combining these multiple resistance loci using breeding, however, is challenging and therefore, time-consuming and unpractical.

TABLE 1

Chromosomal location of previously reported QTLs conferring resistance to *Meloidogyne incognita* or *Meloidogyne javanica*. No QTLs have been described that confer resistance to *Meloidogyne arenaria.*

| Source | Chr | Pos. (cM) | 1.5 LoD | Remarks |
|---|---|---|---|---|
| Brasilia | 1 | 67 | 52-75 | |
| | 8 | 42 | 42-56 | Co-localizes with Mj-1 locus |
| Homs | 1 | 35 | 23-65 | |
| | 2 | 43 | 4-66 | |
| | 2 | 63 | 61-67 | |
| | 8 | 42 | 41-44 | Co-localizes with Mj-1 locus |
| | 9 | 4 | 4-22 | |
| | 9 | 10 | 4-13 | |
| SFF | 4 | 33 | 15-57 | |
| | 8 | 42 | 27-59 | Co-localizes with Mj-1 |

Explanation of abbreviations used: Chr=chromosome; Pos. is the genomic position in centimorgan (cM); and 1.5 LoD is the 1.5-LOD support interval (the region where the LOD score is within 1.5 of its maximum) and indicates the most plausible location for the QTL Hence, there is a need for a new genomically encoded resistance gene that confers resistance to the tropical root-knot nematode species *Meloidogyne incognita* as a monogenic dominant inherited trait. Preferably, such a resistance gene would confer resistance to not just *Meloidogyne incognita*, but to multiple tropical root-knot nematodes species, in particular *Meloidogyne arenaria* and *Meloidogyne incognita* as such a genomically encoded resistance could easily be combined with resistances to *Meloidogyne javanica* known in the prior art to yield a carrot plant resistant to all three tropical root-knot nematode species. Most preferably, a new genomically encoded resistance gene confers resistance to all three tropical root-knot nematode species, i.e., *Meloidogyne incognita, Meloidogyne arenaria* and *Meloidogyne javanica.*

SUMMARY OF THE INVENTION

Considering the above, it is an object of the present invention amongst other objects, to provide carrot plants, or *Daucus carota* plants, resistant to the tropical root-knot nematode species *Meloidogyne incognita*; more preferably, to the tropical root-knot nematode species *Meloidogyne incognita* and *Meloidogyne arenaria*; and most preferably, to all three tropical root-knot nematodes *Meloidogyne incognita, Meloidogyne arenaria* and *Meloidogyne javanica.*

The present invention meets the above object, amongst other objects, as outlined in the appended claims.

DESCRIPTION OF THE INVENTION

Specifically, this object, amongst other objects, is achieved, according to a first aspect, by providing a carrot plant resistant to tropical root-knot nematodes, comprising on chromosome 4 of said carrot plant a first tropical root-knot nematode resistance providing genomic fragment, wherein said first genomic fragment comprises a nucleic acid sequence selected from the group consisting of SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21 and SEQ ID No. 23. The indefinite article "a" or "an" can be used interchangeably with the phrases "one or more" or "at least one". As such, the word "a" should be understood to mean one, two, three, four, five, six, or more, or all. Preferably, the first tropical root-knot nematode resistance providing genomic fragment on chromosome 4 comprises SEQ ID No. 9; more preferably SEQ ID No. 9 and SEQ ID No. 11; more preferably SEQ ID No. 5, SEQ ID No. 7, SEQ ID No. 9 and SEQ ID No. 11; even more preferably SEQ ID No. 1, SEQ ID No. 3, SEQ ID No. 5, SEQ ID No. 7, SEQ ID No. 9 and SEQ ID No. 11; yet even more preferably SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19 and SEQ ID No. 21; and most preferably SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21, and SEQ ID No. 23. The first tropical root-knot resistance providing genomic fragment is not comprised of SEQ ID No. 2, SEQ ID No. 4, SEQ ID No. 6, SEQ, ID No. 8, SEQ ID No. 10, SEQ ID No. 12, SEQ ID No. 14, SEQ ID No. 16, SEQ ID No. 18, SEQ ID No. 20, SEQ ID No. 22, and SEQ ID No. 24.

Tropical root-knot nematode is defined as a group consisting of three tropical root-knot nematode species: *Meloidogyne incognita, Meloidogyne arenaria* and *Meloidogyne javanica*; preferably, *Meloidogyne incognita* and *Meloidogyne arenaria*; most preferably, *Meloidogyne incognita.*

Carrot plant means a plant of the species *Daucus carota*; preferably, a cultivated carrot plant; most preferably, a commercially cultivated carrot plant.

Alternatively, this object, amongst other objects, is achieved by providing a tropical root-knot nematode resistant carrot plant comprising two tropical root-knot nematode resistance providing genomic fragments, wherein a first tropical root-knot resistance providing genomic fragment is located on chromosome 4 and comprises a nucleic acid sequence selected from the group consisting of SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21 and SEQ ID No. 23; and wherein, a second tropical root-knot resistance providing genomic fragment is selected from the group consisting of SEQ ID No. 25, SEQ ID No. 27, SEQ ID No. 29, SEQ ID No. 31, SEQ ID No. 33, SEQ ID No. 35, SEQ ID No. 37 and SEQ ID No. 39. Preferably, the first tropical root-knot nematode resistance providing genomic fragment on chromosome 4 comprises SEQ ID No. 9; more preferably SEQ ID No. 9 and SEQ ID No. 11; more preferably SEQ ID No. 5, SEQ ID No. 7, SEQ ID No. 9 and SEQ ID No. 11; even more preferably SEQ ID No. 1, SEQ ID No. 3, SEQ ID No. 5, SEQ ID No. 7, SEQ ID No. 9 and SEQ ID No. 11; yet even more preferably SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19 and SEQ ID No. 21; and most preferably SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21, and SEQ ID No. 23. The first tropical root-knot resistance providing genomic fragment is not comprised of SEQ ID No. 2, SEQ ID No. 4, SEQ ID No. 6, SEQ, ID No. 8, SEQ ID No. 10, SEQ ID No. 12, SEQ ID No. 14, SEQ ID No. 16, SEQ ID No. 18, SEQ ID No. 20, SEQ ID No. 22, and SEQ ID No. 24. Preferably, the second tropical root-knot nematode resistance providing genomic fragment on chromosome 8 comprises SEQ ID No. 31, more preferably SEQ ID No. 31 and SEQ ID No. 33; more preferably SEQ ID No. 31, SEQ ID No. 33, SEQ ID No. 35 and SEQ ID No. 37; even more preferably SEQ ID No. 31, SEQ ID No. 33, SEQ ID No. 35, SEQ ID No. 37 and SEQ ID No. 39; most preferably SEQ ID No. 25, SEQ ID No. 27, SEQ ID No. 29, SEQ ID No. 31, SEQ ID No. 33, SEQ ID No. 35, SEQ ID No. 37 and SEQ ID No. 39.

Hence, in one preferred embodiment, the tropical root-knot resistant carrot plant comprises SEQ ID No. 9 and SEQ ID No. 31; more preferably SEQ ID No. 9, SEQ ID No. 11, SEQ ID No. 31 and SEQ ID No. 33; more preferably SEQ ID No. 5, SEQ ID No. 7, SEQ ID No. 9, SEQ ID No. 11, SEQ ID No. 31 and SEQ ID No. 33; even more preferably SEQ ID No. 1, SEQ ID No. 3, SEQ ID No. 5, SEQ ID No. 7, SEQ ID No. 9, SEQ ID No. 11, SEQ ID No. 31, SEQ ID No. 33, SEQ ID No. 35 and SEQ ID No. 37; yet even more preferably SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21, SEQ ID No. 31, SEQ ID No. 33, SEQ ID No. 35, SEQ ID No. 37 and SEQ ID No. 39; and most preferably SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21, SEQ ID No. 23, SEQ ID No. 25, SEQ ID No. 27, SEQ ID No. 29, SEQ ID No. 31, SEQ ID No. 33, SEQ ID No. 35, SEQ ID No. 37 and SEQ ID No. 39.

According to a preferred embodiment of the present invention, the first tropical root-knot nematode resistance providing genomic fragment is obtained, obtainable, or is from a carrot plant of which representative seed has been deposited at NCIMB (National Collections of Industrial, Food and Marine Bacteria; 5 NCIMB Limited, Ferguson Building; Craibstone Estate, Bucksburn Aberdeen, Scotland, AB21 9YA United Kingdom) on 9 Jun. 2021 under deposit number NCIMB 43792.

According to another preferred embodiment, the present carrot plant is cytoplasmic male sterile (CMS).

According to yet another preferred embodiment, the present carrot plant is a hybrid carrot plant, more preferably a sterile hybrid carrot plant and most preferably a male sterile hybrid carrot plant, e.g., cytoplasmic male sterile.

The present invention further relates to a method for identifying a tropical root-knot nematode resistance providing genomic fragment as found in the present carrot plant. The method comprises the steps of isolating or providing genomic nucleic acid of a carrot plant and identifying in the genomic nucleic acid a first tropical root-knot nematode resistance providing genomic fragment on chromosome 4 by detecting a nucleic acid sequence selected from the group consisting of SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21 and SEQ ID No. 23.

Preferably, the present method comprises an optional step of further identifying in the genomic nucleic acid a second tropical root-knot nematode resistance providing genomic fragment on chromosome 8 by detecting a nucleic acid sequence selected from the group consisting of SEQ ID No. 25, SEQ ID No. 27, SEQ ID No. 29, SEQ ID No. 31, SEQ ID No. 33, SEQ ID No. 35, SEQ ID No. 37, and SEQ ID No. 39.

Several common genotyping methods exist for detecting a single nuclear polymorphism (SNP) in a genomic sequence, including PCR-based methods, direct hybridization, fragment analysis, and sequencing. An example of a method suitable for detecting a genomic sequence is isolating DNA from available plant material (e.g., from a piece of a leaf from a plant, or a seed), followed by nucleic acid amplification of isolated DNA (e.g., using PCR) and detecting the presence of said genomic sequence (e.g., by sequencing, measuring fluorescence, or visualizing and analysing PCR amplification using agarose gel electrophoresis).

Additionally, the present invention relates to a method for providing a carrot plant of the invention comprising the steps of:

a) obtaining a carrot plant not comprising a first tropical root-knot nematode resistance providing genomic fragment on chromosome 4 of the carrot plant;
b) crossing the carrot plant with a carrot plant comprising a first tropical root-knot nematode resistance providing genomic fragment on chromosome 4 of the carrot plant; obtaining a seed from said cross and germinating the seed to obtain a carrot plant;
c) isolating genomic nucleic acid from the carrot plant and identifying in the genomic nucleic acid a first tropical root-knot nematode resistance providing genomic fragment on chromosome 4 of the carrot plant by detecting a nucleic acid sequence selected from the group consisting of SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21 and SEQ ID No. 23.

Preferably, the present method comprises an optional step of further identifying in the genomic nucleic acid a second tropical root-knot nematode resistance providing genomic fragment on chromosome 8 of the carrot plant by detecting a nucleic acid sequence selected from the group consisting of SEQ ID No. 25, SEQ ID No. 27, SEQ ID No. 29, SEQ ID No. 31, SEQ ID No. 33, SEQ ID No. 35, SEQ ID No. 37, and SEQ ID No. 39.

The present invention also relates to a method of producing a carrot plant of the invention comprising the steps of obtaining a carrot plant not comprising a first tropical root-knot nematode resistance providing genomic fragment on chromosome 4 of said carrot plant; introducing in said carrot plant a first tropical root-knot nematode resistance providing genomic fragment as found in a carrot plant of the present invention, wherein said genomic fragment is not introduced by means of an essentially biological process.

Mutagenesis, transformation with *Agrobacterium* or CRISPR/Cas can be used to introduce a first tropical root-knot nematode resistance providing genomic fragment by means of a non-essentially biological process.

Suitable mutagenesis methods comprise chemical mutagenesis (e.g., using ethyl methanesulfonate (EMS), N-methyl-N-nitrosourea (MNU), N-ethyl-N-nitrosourea (ENU), sodium azide (NaN3), methylnitrosoguanidine (MNNG), diethyl sulfonate (DES), TILLING, or mutagenesis by generating reactive oxygen species) and radiation mutagenesis (e.g., using UV radiation or ion beam radiation). Mutagenesis can lead to one or more mutations located in the coding sequence (mRNA, cDNA or genomic sequence) or in the associated non-coding sequence and/or regulatory sequence regulating the level of expression of the coding sequence. The presence of one or more mutations (e.g., insertion, inversion, deletion and/or replacement of one or more nucleotide(s)) may lead to the encoded protein having a new or altered functionality (gain of function), reduced functionality (reduced function) or no functionality (loss-of-function), e.g., due to the protein being truncated or having an amino acid sequence wherein one or more amino acids are deleted, inserted or replaced. Such changes may lead to the protein having a different 3D structure or conformation, being targeted to a different sub-cellular compartment, having one or more modified catalytic domains, having a modified binding activity to nucleic acids or proteins, etcetera.

Alternatively, the resistance according to the invention can be introduced in a plant cell by transformation (e.g., using *Agrobacterium tumefaciens*). Genomic fragments can be amplified by long-range PCR amplifications, de novo synthesized, or isolated from gels or columns (e.g., after restriction digestion). The resulting fragments can be reassembled (e.g., in yeast) or introduced in an expression vector, subsequently transformed into carrot plant cells and allowed to integrate or recombine with the carrot plant genome. The fragment may be introduced in a single step or in a series of transformations ultimately resulting in a carrot plant comprising the resistance of the present invention.

Alternatively, the CRISPR/Cas9 system can be used to introduce tropical root-knot nematode resistance in a carrot plant by enabling robust and precise targeted genome modifications, as well as CRISPR-based screening, e.g., using pooled gRNA libraries with complete coverage and distribution over the carrot genome, and whole genome mutagenesis.

According to a second aspect, the present invention also relates to a seed capable of providing a plant of the present invention Seeds can be coated, coloured, washed, polished, encrusted, pelleted, primed or undergo a combination of treatments. Coated seeds are covered by a relatively thin layer of polymer supplied to the seed; to this polymer fungicides or insecticides can be added to protect the seed against soil borne pathogens and insect damage. Additionally, a dye can be added. This added colour gives the farmer the opportunity to check for correct drilling of the seeds. Alternatively, also other beneficial compounds can be added as micronutrients or beneficial micro-organisms promoting the growth of the young seedlings. Encrusted seeds are not only covered by a polymer with or without extra substances, as described above, but the seeds are provided with a smooth surface as well. This makes drilling easier, and the added weight enables a more precise direct drilling of the seeds. Polishing removes the outermost layer of the seed, so that the seed assumes a more rounded form. Polishing and washing promotes germination of the seed. With pelleting the seeds are covered with more material, e.g., polymer bound clay, to produce a regularly shaped, round pellet. This pellet, besides having protecting substances described above, can be constructed in such a way that it will melt or split after water uptake. Priming or pre-germination is a treatment in which seeds are given enough moisture to initiate germination of the embryo inside the seed. This results in a faster emergence of the seedling, a higher emergence rate and better growth. It is believed that priming leads to a better root system and faster growth.

According to a third aspect, the present invention further relates to a plant cell, a protoplast, a plant organ, plant tissue, edible parts, pollen, microspores, ovaries, ovules, egg cells, callus, suspension culture, somatic embryos, embryos, or plant parts of the present plants resistant to tropical root-knot nematodes. Plant parts include, but are not limited to, the shoot, the stalk, the stem, leaves, blossoms, inflorescence, roots, fruits, and cuttings.

Additionally, the present invention relates to use of a nucleic acid sequence selected from the group consisting of SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21 and SEQ ID No. 23 for identifying or providing a first tropical root-knot nematode resistance providing genomic fragment as found in a carrot plant of which representative seed has been deposited under deposit number NCIMB 43792. The indefinite article "a" or "an" can also here be used interchangeably with the phrases "one or more" or "at least one". As such, the word "a" should be understood to mean one, two, three, four, five, six, or more, or all. The nucleic acid sequences are closely linked to the first tropical root-knot nematode resistance providing genomic fragment and can be used as molecular markers, e.g., in molecular marker-assisted breeding. Molecular marker-assisted breeding greatly increases efficiency and precision of plant breeding, and includes several modern breeding strategies, including marker-assisted selection, marker-assisted backcrossing, marker-assisted recurrent selection, and genome-wide selection or genomic selection.

The present invention also relates to nucleic acid sequences which co-segregate with a first tropical root-knot nematode providing genomic fragment as present in deposit number NCIMB 43792, which nucleic acid sequences are selected from the group consisting of SEQ ID No. 1, SEQ ID No. 3, SEQ ID No. 5, SEQ ID No. 7, SEQ ID No. 9, SEQ ID No. 11, SEQ ID No. 13, SEQ ID No. 15, SEQ ID No. 17, SEQ ID No. 19, SEQ ID No. 21, and SEQ ID No. 23.

The present invention will be further detailed in the following examples.

EXAMPLES

Example 1: Mutagenesis of Carrot Plants to Introduce Tropical Root-Knot Nematode Resistance Random mutagenesis followed by forward screening is a useful method for identifying mutant carrot plants with resistance to tropical root-knot nematodes. A mutagenized library can be generated by subjecting seeds to a step of mutagenesis, preferably random mutagenesis. Such a step may comprise, but is not limited to, the treatment of a pool of 100,000 to 200,000 seeds with a chemical mutagen, or a mixture of chemical mutagens, e.g., 0.25% EMS for 16 hours at room temperature; alternatively, radiation can be used (e.g., gamma-radiation from a radioactive Cobalt-60 source). Preferably, only a mildly mutagenized library (fewer than 1% of all genes contain a mutation in a coding region) is generated. Nevertheless, the mutagenesis step will lead to the loss of germination in some seeds. In contrast to irradiation, which can lead to mutations varying from single base substitutions or deletions to large deletions, EMS produces predominantly random point mutations by nucleotide substitution, particularly by guanine alkylation.

The mutagenized seeds can be sown and propagated in a field using standard practices. The mutagenized seed will generate plants that each have a particular set of mutations. Plants can be harvested in pools and viable seeds can be sown again (F1 population). To obtain an F1S1 population seeds can be collected from the F1 plants after selfing. As the mutations will segregate in an F1S1 population, the resistance in this population can be evaluated and used to map the resistance against tropical root-knot nematodes.

Example 2. General Protocol for Assessing Resistance

Four-week-old carrot plants are transplanted into pots filled with fine white sand. One week after transplanting, plants are tested for tropical root-knot nematode resistance by injecting 1 ml inoculation medium containing 2000-2500 tropical root-knot nematode eggs/ml next to the root system at a depth of 0.5 cm. Plants are not watered for 48 h after inoculation to prevent flushing of tropical root-knot nematode eggs.

Eight to ten weeks after inoculation plants are assessed for severity of tropical root-knot nematode infection. Plants are uprooted and the root system is flushed with tap water to remove the potting soil and fine white sand. After washing, plants are placed in 10% carmine staining solution for five minutes. The number of galls is subsequently counted under a microscope. The maximum number of galls counted per plant is 50. It is carefully checked that the susceptible control plants indeed show the expected symptoms of tropical root-knot nematode infection and that the resistant controls show no infection. Per accession the average number of galls is calculated (AVG), as well as the standard deviation (STD), the percentage of plants with only 2 galls or less (%≤2) or 5 galls or less (%≤5), which are all indicative values for the level of resistance.

Example 3. Results of Assessment for Resistance Against Tropical Root-Knot Nematode Resistance

TABLE 2

Several sources of resistance were tested with different populations, including sources described in literature. Mi-WU-1 is a *Meloidogyne incognita* population obtained from the nematology group at Wageningen University. MAU is a *Meloidogyne arenaria* population originating from North America. A minimum of 10 plants were tested per condition.

| | Population | AVG | STD | % ≤2 | % ≤5 |
|---|---|---|---|---|---|
| Sus 1 | Mi-WU-1 | 50.0 | 0.0 | 0% | 0% |
| Sus 2 | Mi-WU-1 | 42.1 | 13.8 | 0% | 0% |
| Res | Mi-WU-1 | 2.4 | 2.8 | 50% | 88% |
| SFF | Mi-WU-1 | 7.3 | 7.6 | 32% | 56% |
| Homs | Mi-WU-1 | 12.5 | 11.4 | 15% | 32% |
| Sus 1 | MAU | 16.0 | 8.5 | 0% | 13% |
| Sus 2 | MAU | 35.6 | 11.2 | 0% | 0% |
| Res | MAU | 0.2 | 0.7 | 94% | 100% |
| SFF | MAU | 0.6 | 0.7 | 100% | 100% |
| Homs | MAU | 0.2 | 0.4 | 100% | 100% |

Explanation of abbreviations used: AVG is the average number of galls counted per plant under a microscope; STD is the standard deviation of the number of galls counted per plant under a microscope; %≤2 is the percentage of plants that had 2 or fewer galls; %≤5 is the percentage of plants that had 5 or fewer galls.

Example 4: Molecular Characterization of Genomic DNA and Mapping of the Resistance Genes Applying the genetic resource for resistance, here referred to as Res, an F1S1 population was made by crossing the source of resistance to the sus 1 carrot line, after which the resulting F1 plant was self-pollinated.

At least 2000 seeds were harvested from the F1S1 generation of a cross between the distinctive source of resistance and the sus 1 carrot line. To perform a QTL mapping, 240 plants of the cross were tested with the Mi-WU-1 isolate. From each individual plant, leaf material was used for DNA isolation and successive marker analysis.

Using SNP markers covering the entire genome, a QTL was found on chromosome 4 (C4). This QTL is defined by the SNP markers listed in the table below.

TABLE 3

SNPs for the detection of the tropical root-knot nematode resistance providing genomic fragment on chromosome 4. The genomic position of each SNP was determined using the published genome assembly PRJNA268187 *Daucus carota* Ver2.

| SNP | ID | Chromosome | Position on chromosome (bp) | Allele linked to resistance | Alternative allele |
|---|---|---|---|---|---|
| 1 | 9847 | 4 | 10231839 | G | A |
| 2 | 6624 | 4 | 10367643 | C | A |
| 3 | 9848 | 4 | 10375226 | A | G |
| 4 | 9849 | 4 | 10503519 | C | T |
| 5 | 6873 | 4 | 10507269 | C | T |
| 6 | 9850 | 4 | 10627267 | A | G |
| 7 | 6524 | 4 | 10667421 | A | G |
| 8 | 8738 | 4 | 10674185 | T | C |
| 9 | 2281 | 4 | 10705926 | T | G |
| 10 | 8363 | 4 | 10734365 | C | T |
| 11 | 9851 | 4 | 10753940 | T | G |
| 12 | 7147 | 4 | 10957339 | A | G |

TABLE 4

Sequences for the detection of the resistance against tropical root-knot nematodes on chromosome 4. The genomic position of each SNP was determined using the published genome assembly PRJNA268187 *Daucus carota* Ver2. Nucleotide base codes are according to the International Union of Pure and Applied Chemistry (IUPAC) code (see Table 5).

| SEQ ID No. | SNP | Genomic position of SNP* | Nucleic acid sequence |
|---|---|---|---|
| 1 | 1 | CHR4_10231839 | TGTTTGAGACTCWACTCTTCTCCTTTACCAACGAAAGTATTTATTTGTGA[G]CAATCTTTCATGTCAAACCTAGCAAGTACCTTCTCAATATGGCTCTTTTA |
| 2 | 1 | CHR4_10231839 | TGTTTGAGACTCWACTCTTCTCCTTTACCAACGAAAGTATTTATTTGTGA[A]CAATCTTTCATGTCAAACCTAGCAAGTACCTTCTCAATATGGCTCTTTTA |
| 3 | 2 | CHR4_10367643 | TCCTATCTCTCTTCCTCCTCACAATCCTTCCCATTCT[C]CACTCCTTACCAGCCATACCAGACCCAACCACA |
| 4 | 2 | CHR4_10367643 | TCCTATCTCTCTTCCTCCTCACAATCCTTCCCATTCT[A]CACTCCTTACCAGCCATACCAGACCCAACCACA |
| 5 | 3 | CHR4_10375226 | ATTATACTTATACTTGTTTAAATATGTGGTAACTTTGGGTGCCAATCACT[A]GAGCAAATTTTTATGTAAAAGTTGTCAAAAATACAAACAAAGRGAGAGAA |
| 6 | 3 | CHR4_10375226 | ATTATACTTATACTTGTTTAAATATGTGGTAACTTTGGGTGCCAATCACT[G]GAGCAAATTTTTATGTAAAAGTTGTCAAAAATACAAACAAAGRGAGAGAA |
| 7 | 4 | CHR4_10503519 | CTTCACAACTATTTACHAAGTAATTTAAAACTTCTTTAATCTGTGAAGCT[C]GATATCTTATTGCTTTAACTCCTATAACCCGACWTTCTCAACATATTTCT |
| 8 | 4 | CHR4_10503519 | CTTCACAACTATTTACHAAGTAATTTAAAACTTCTTTAATCTGTGAAGCT[T]GATATCTTATTGCTTTAACTCCTATAACCCGACWTTCTCAACATATTTCT |
| 9 | 5 | CHR4_10507269 | CGACCAATGATATCAGTTTTTTCGACGATAATAATCT[C]GGGTCGTTAGAATTGGATTCTCTCTGGACTTGA |
| 10 | 5 | CHR4_10507269 | CGACCAATGATATCAGTTTTTTCGACGATAATAATCT[T]GGGTCGTTAGAATTGGATTCTCTCTGGACTTGA |
| 11 | 6 | CHR4_10627267 | TTATATACTGTATAAAACAATGATTAGTGCAACAAAAATTAGTGATAGTC[A]TAGTTATAAATACTGGTAAGGAAACTAGTTTTTAGTTTGTATTTAAGAGT |
| 12 | 6 | CHR4_10627267 | TTATATACTGTATAAAACAATGATTAGTGCAACAAAAATTAGTGATAGTC[G]TAGTTATAAATACTGGTAAGGAAACTAGTTTTTAGTTTGTATTTAAGAGT |
| 13 | 7 | CHR4_10667421 | ATCCGTCAATTAGAAAAAGTTAAAAAACACTCTCTCT[A]GACACCCATTCTCATTTGAAGCAACACGTGATG |
| 14 | 7 | CHR4_10667421 | ATCCGTCAATTAGAAAAAGTTAAAAAACACTCTCTCT[G]GACACCCATTCTCATTTGAAGCAACACGTGATG |
| 15 | 8 | CHR4_10674185 | GCTACAACTTTTATCTTTTTCAGTCTTTACATGAAGTAMTAGCCGTAAAT[T]TTKCAAGCCAAAGGTGCAACACATTGTAGACTCGACAATATCTTTCACTC |
| 16 | 8 | CHR4_10674185 | GCTACAACTTTTATCTTTTTCAGTCTTTACATGAAGTAMTAGCCGTAAAT[C]TTKCAAGCCAAAGGTGCAACACATTGTAGACTCGACAATATCTTTCACTC |
| 17 | 9 | CHR4_10705926 | CACTTGTCCTGAAGAATGTCAAGGCAAATATTCCCATACTGGTCAACATT[T]GGATGGAAGCACATTGTCTCAAACTTCACTTGGGGAGGCTTGAAAGGATA |
| 18 | 9 | CHR4_10705926 | CACTTGTCCTGAAGAATGTCAAGGCAAATATTCCCATACTGGTCAACATT[G]GGATGGAAGCACATTGTCTCAAACTTCACTTGGGGAGGCTTGAAAGGATA |
| 19 | 10 | CHR4_10734365 | TAAGGCTTGCRTTGGMTTAAARAGTTGCAGCATCGACGTATCAGTGTCAA[C]TTTTGGGAATCCGTGTAGAGGAGTTACAAAGAGTTTAGCAGTAGAAGCWT |
| 20 | 10 | CHR4_10734365 | TAAGGCTTGCRTTGGMTTAAARAGTTGCAGCATCGACGTATCAGTGTCAA[T]TTTTGGGAATCCGTGTAGAGGAGTTACAAAGAGTTTAGCAGTAGAAGCWT |
| 21 | 11 | CHR4_10753940 | ATGACACCAACACGGTGAAAGTCAGTGTATCTGGCCTTTTGGAGGTGGAT[T]TGAAGGTGACTCCAATAAAAGAAAAGGAAAACAAGGTGCACAACTACCAG |
| 22 | 11 | CHR4_10753940 | ATGACACCAACACGGTGAAAGTCAGTGTATCTGGCCTTTTGGAGGTGGAT[G]TGAAGGTGACTCCAATAAAAGAAAAGGAAAACAAGGTGCACAACTACCAG |
| 23 | 12 | CHR4_10957339 | CCATACCCATTCTTTTGAAATGAAAATGCAAAACAGA[A]GTCTTCCAGTAGCTCTCTACCTGCATTTGACAA |
| 24 | 12 | CHR4_10957339 | CCATACCCATTCTTTTGAAATGAAAATGCAAAACAGA[G]GTCTTCCAGTAGCTCTCTACCTGCATTTGACAA |

*CHR4 = chromosome 4

TABLE 5

Nucleotide base codes according to the International Union of Pure and Applied Chemistry (IUPAC) code.

| Symbol | Nucleotide Base |
|---|---|
| A | Adenine |
| C | Cytosine |
| G | Guanine |
| T | Thymine |
| N | A or C or G or T |
| M | A or C |

TABLE 5-continued

Nucleotide base codes according to the International Union of Pure and Applied Chemistry (IUPAC) code.

| Symbol | Nucleotide Base |
|---|---|
| R | A or G |
| W | A or T |
| S | C or G |
| Y | C or T |
| K | G or T |
| V | Not T |
| H | Not G |
| D | Nor C |
| B | Not A |

Example 5: QTL on C4 is not Allelic to Resistance on Chromosome 4 Previously Discovered in SFF Several individual plants from the SPF line were used to make crosses with the sus 1 carrot line. These individual plants were also self-pollinated. The progeny was tested for resistance. The selfings of the individual plants from SFF still show a level of resistance, while all hybrids are fully susceptible.

In contrast, when similar crosses were made with Res plants, the progeny of the selfings showed a high level of resistance. Also, hybrids made by crossing with the susceptible sus 1 and sus 2 carrot lines still showed a level of resistance.

From these tests, it is clear that the previously described QTL on C4 derived from SFF does not provide any level of resistance when present in a heterozygous form, in contrast to the QTL derived from Res.

TABLE 6

Several selfings of SFF and Res as well as crosses with susceptible carrot lines were tested with a *Meloidogyne incognita* population obtained from the nematology group at Wageningen University (Mi-WU-1).

| Name | # plants | AVG | STD | % ≤2 | % ≤5 |
|---|---|---|---|---|---|
| Res*Res | 6 | 1.8 | 0.8 | 83% | 100% |
| Sus 1*Sus 1 | 8 | 50.0 | 0.0 | 0% | 0% |
| Sus 2*Sus 2 | 8 | 42.1 | 13.8 | 0% | 0% |
| Sus 1*Res (C4) | 235 | 15.1 | 9.6 | 2% | 15% |
| SFF*SFF | 10 | 8.0 | 4.1 | 10% | 20% |
| Sus 1*SFF | 14 | 50.0 | 0.0 | 0% | 0% |

Explanation of abbreviations used: #plants is the number of plants tested, AVG is the average number of galls counted per plant under a microscope; STD is the standard deviation of the number of galls counted per plant under a microscope; %≤2 is the percentage of plants that had 2 or fewer galls; %≤5 is the percentage of plants that had 5 or fewer galls.

Example 6: QTL on C4 can be Combined with QTL on C8 to Further Enhance Resistance Several resistances against *Meloidogyne javanica* and *Meloidogyne incognita* have been previously described in literature (e.g., Parsons et al. 2015). As the QTL on chromosome 8 (C8), referred to as Mj-1, has been described as a monogenic dominant trait that imparts resistance to *Meloidogyne javanica* and a partial resistance, plants carrying a tropical root-knot nematode resistance providing genomic fragment on C4 and C8 were combined and tested for resistance to determine whether this provided an even more robust resistance to tropical root-knot nematodes.

The tests showed that the resistance against tropical root-knot nematodes was further improved by combining the QTLs on C4 and C8.

TABLE 7

Carrot plants with a QTL on C4, C4 and C8 and only C8 were tested for root-knot nematode resistance. Mi-WU-1 is a *Meloidogyne incognita* population obtained from the nematology group at Wageningen University. MAU is a *Meloidogyne arenaria* population originating from North America.

| ID | Locus | Isolate | #plants | AVG | STD | % ≤2 | % ≤5 |
|---|---|---|---|---|---|---|---|
| Y9380 | C4 | Mi-WU-1 | 89 | 0.8 | 2.9 | 93 | 99 |
| Y9381 | C4, C8 | Mi-WU-1 | 24 | 0.1 | 0.4 | 100 | 100 |
| Y9383 | C8 | Mi-WU-1 | 176 | 23.0 | 16.1 | 4 | 10 |
| Y9380 | C4 | MAU | 68 | 1.9 | 3.7 | 74 | 97 |
| Y9381 | C4, C8 | MAU | 18 | 0.2 | 0.7 | 95 | 100 |
| Y9383 | C8 | MAU | 176 | 7.0 | 9.3 | 42 | 61 |

Explanation of abbreviations used: #plants is the number of plants tested, AVG is the average number of galls counted per plant under a microscope; STD is the standard deviation of the number of galls counted per plant under a microscope; %≤2 is the percentage of plants that had 2 or fewer galls; %≤5 is the percentage of plants that had 5 or fewer galls SNP markers were used to detect the tropical root-knot resistance providing genomic fragment on C8 and to identify and provide plants carrying this resistance providing fragment.

TABLE 8

SNPs for the detection of the tropical root-knot nematode resistance providing genomic fragment on chromosome 8. The genomic position of each SNP was determined using the published genome assembly PRJNA268187 *Daucus carota* Ver2.

| SNP | ID | Chromosome | Position on chromosome (bp) | Allele linked to resistance | Alternative allele |
|---|---|---|---|---|---|
| 13 | 7136 | 8 | 17676345 | C | G |
| 14 | 6692 | 8 | 17781631 | G | A |
| 15 | 4421 | 8 | 17968674 | C | A |
| 16 | 6419 | 8 | 18836406 | G | C |
| 17 | 5095 | 8 | 21101599 | T | C |
| 18 | 4255 | 8 | 21235813 | A | G |
| 19 | 5020 | 8 | 21254357 | T | C |
| 20 | 4441 | 8 | 21422127 | C | T |

TABLE 9

Sequences for the detection of the resistance against tropical root-knot nematodes on chromosome 8. The genomic position of each SNP was determined using the published genome assembly PRJNA268187 *Daucus carota* Ver2. Nucleotide base codes are according to the International Union of Pure and Applied Chemistry (IUPAC) code (see Table 5).

| SEQ ID No. | SNP | Genomic position of SNP* | Nucleic acid sequence |
|---|---|---|---|
| 25 | 13 | CHR8_17676345 | AAACATTAAACTTGGCGGATGATGATATATATAATGC[C]GTGCTACTTGTTGCAGCTGCTTATAATCACTTT |

TABLE 9-continued

Sequences for the detection of the resistance against tropical root-knot nematodes on chromosome 8. The genomic position of each SNP was determined using the published genome assembly PRJNA268187 *Daucus carota* Ver2. Nucleotide base codes are according to the International Union of Pure and Applied Chemistry (IUPAC) code (see Table 5).

| SEQ ID No. | SNP | Genomic position of SNP* | Nucleic acid sequence |
|---|---|---|---|
| 26 | 13 | CHR8_ 17676345 | 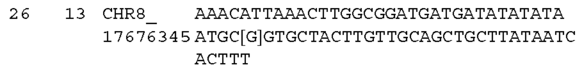 AAACATTAAACTTGGCGGATGATGATATATATA ATGC[G]GTGCTACTTGTTGCAGCTGCTTATAATC ACTTT |
| 27 | 14 | CHR8_ 17781631 | GATCGAAGGGGGTGCGGCCAGAGGTCTTTGCCC GAGC[G]TATGCCCGTGTCTTCTCCTCGTTACTTG TCCTT |
| 28 | 14 | CHR8_ 17781631 | GATCGAAGGGGGTGCGGCCAGAGGTCTTTGCCC GAGC[A]TATGCCCGTGTCTTCTCCTCGTTACTTG TCCTT |
| 29 | 15 | CHR8_ 17968674 | CTCTCGGRACCCAACCAATTACCCTACGAACTT TCTC[C]TCGAAGAGTACTACACATGTTTTTGCTG CCTCA |
| 30 | 15 | CHR8_ 17968674 | CTCTCGGRACCCAACCAATTACCCTACGAACTT TCTC[A]TCGAAGAGTACTACACATGTTTTTGCTG CCTCA |
| 31 | 16 | CHR8_ 18836406 | GAGAATCTGCCGTACGGCGTGTTCAAGCCTGAC GAAT[G]TTCGGCACCTCGACCTGGCGTTGCTAT CGGRGA |
| 32 | 16 | CHR8_ 18836406 | GAGAATCTGCCGTACGGCGTGTTCAAGCCTGAC GAAT[C]TTCGGCACCTCGACCTGGCGTTGCTAT CGGRGA |
| 33 | 17 | CHR8_ 21101599 | GCCAAAGGCTACTACAAAGTGGTTGCAAGTTTC AAAA[T]TGATGCACAAGGGTGCTGTGTCAAGTG AAGATC |
| 34 | 17 | CHR8_ 21101599 | GCCAAAGGCTACTACAAAGTGGTTGCAAGTTTC AAAA[C]TGATGCACAAGGGTGCTGTGTCAAGTG AAGATC |
| 35 | 18 | CHR8_ 21235813 | GAAAATATCATCGCCACGAGATAATTTTTGCTG ATCA[A]CAAAGACTTGAGAGTAACATTCGACTT CCCGTG |
| 36 | 18 | CHR8_ 21235813 | GAAAATATCATCGCCACGAGATAATTTTTGCTG ATCA[G]CAAAGACTTGAGAGTAACATTCGACTT CCCGTG |
| 37 | 19 | CHR8_ 21254357 | TTTTACATAGTTACAATTAGAAATTCAGATCCC ACCT[T]TTAGACTCCAACCTCTCCGGCTAACTTG AAAGG |
| 38 | 19 | CHR8_ 21254357 | TTTTACATAGTTACAATTAGAAATTCAGATCCC ACCT[C]TTAGACTCCAACCTCTCCGGCTAACTTG AAAGG |
| 39 | 20 | CHR8_ 21422127 | TACAACTCGATGCTTATATATCACGAAAAGAAC TCTT[C]AAGGCAGAAGCAAAATATTGGAATGAA ATAATA |
| 40 | 20 | CHR8_ 21422127 | TACAACTCGATGCTTATATATCACGAAAAGAAC TCTT[T]AAGGCAGAAGCAAAATATTGGAATGAA ATAATA |

*CHR8 = chromosome 8

Example 7: Introduction of Tropical Root-Knot Resistance into a Carrot Plant Using *Agrobacterium*

Transformation of plants using the *Agrobacterium tumefaciens* system is commonly used to generate plants resistant to pathogens by introducing resistance genes in plants. The *Agrobacterium tumefaciens* system can also be used to introduce a tropical root-knot resistance providing genomic fragment according to the present invention. Such a fragment is isolated from gels or columns after restriction digestion of a carrot plant comprising a first tropical root-knot nematode resistance providing genomic fragment. The digested fragment can be introduced in a single step or in a series of transformations using *Agrobacterium tumefaciens* into carrot plant cells. After transformation, stable transformants comprising the resistance of the present invention will be selected by performing a disease test or by determining the presence of the resistance providing genomic fragment using molecular markers.

Deposit Information

Seed samples of the sources of resistance mentioned above have been deposited at the NCIMB (Ferguson Building, Craibstone Estate, Bucksburn, Aberdeen, Scotland, AB21 9YA) on 9 Jun. 2021 as NCIMB 43792.

The invention claimed is:

1. A carrot plant resistant to tropical root-knot nematodes, comprising on chromosome 4 of said carrot plant a first tropical root-knot nematode resistance providing genomic fragment, wherein said first genomic fragment comprises SEQ ID Nos. 1, 3, 5, 7, 9, 11, 13, 15, 17, 19, 21 and 23.

2. The carrot plant according to claim 1, further comprising a second tropical root-knot nematode resistance providing genomic fragment on chromosome 8 of the carrot plant, wherein said second genomic fragment comprises SEQ ID Nos. 25, 27, 29, 31, 33, 35, 37 and 39.

3. The carrot plant according to claim 1 wherein a first tropical root-knot nematode resistance providing genomic fragment is obtained from a carrot plant of which representative seeds are deposited under deposit number NCIMB 43792.

4. The carrot plant according to claim 1, wherein said carrot plant is cytoplasmic male sterile (CMS).

5. The carrot plant according to claim 1, wherein said carrot plant is a hybrid plant.

6. The carrot plant according to claim 1, wherein said carrot plant is a carrot plant of which representative seeds are deposited under deposit number NCIMB 43792.

7. A method for identifying a tropical root-knot nematode resistance providing genomic fragment comprising the steps of:

a) isolating or providing a genomic nucleic acid of a carrot plant;

b) identifying in said genomic nucleic acid a first tropical root-knot nematode resistance providing genomic fragment on chromosome 4 by detecting SEQ ID Nos. 1, 3, 5, 7, 9, 11, 13, 15, 17, 19, 21 and 23; and c) optionally, further identifying in said genomic nucleic acid a second tropical root-knot nematode resistance providing genomic fragment on chromosome 8 by detecting SEQ ID Nos. 25, 27, 29, 31, 33, 35, 37 and 39.

8. A method for providing a tropical root-knot nematode resistant carrot plant comprising the steps of:

a) obtaining a carrot plant not comprising a first tropical root-knot nematode resistance providing genomic fragment on chromosome 4 of said carrot plant;

b) crossing said carrot plant with a carrot plant according to claim 1;

c) obtaining a seed from said cross and germinating said seed to obtain a carrot plant;

d) isolating genomic DNA from said carrot plant and identifying in the genome of said carrot plant SEQ ID Nos. 1, 3, 5, 7, 9, 11, 13, 15, 17, 19, 21 and 23; and e) optionally, further identifying in the genome of said carrot plant SEQ ID Nos. 25, 27, 29, 31, 33, 35, 37, and 39.

9. A method for providing a tropical root-knot nematode resistant carrot plant, comprising the steps of:

a) obtaining a carrot plant not comprising a first tropical root-knot nematode resistance providing genomic fragment on chromosome 4 of said carrot plant; and b) introducing in said carrot plant a first tropical root-knot nematode resistance providing genomic fragment as found in a carrot plant of which representative seed has been deposited under deposit number NCIMB 43792, wherein said genomic fragment is not introduced by means of an essentially biological process.

10. The method according to claim 9, wherein said method for providing comprises the step of mutagenesis, transformation with *Agrobacterium* or CRISPR/Cas.

11. A seed of the carrot plant according to claim 1, comprising a first tropical root-knot nematode resistance providing genomic fragment wherein said first genomic fragment comprises SEQ ID Nos. 1, 3, 5, 7, 9, 11, 13, 15, 17, 19, 21 and 23.

12. The seed according to claim 11, wherein said seed is polished, coated, encrusted, pelleted or primed.

13. A plant part, callus, suspension culture, or clone of a carrot plant according to claim 1.

14. The seed of claim 11, wherein the seed further comprises a second tropical root-knot nematode resistance providing genomic fragment wherein said second genomic fragment comprises SEQ ID Nos. 25, 27, 29, 31, 33, 35, 37, and 39.

* * * * *